(12) United States Patent
Athalin et al.

(10) Patent No.: US 12,303,577 B2
(45) Date of Patent: May 20, 2025

(54) PHOTONIC BARRIER FOR TOPICAL USE, COMPRISING BISMUTH OXIDE COLLOIDS

(71) Applicant: BIONUCLEI, Aix en Provence (FR)

(72) Inventors: Han Athalin, Nantes (FR); Jean-Noël Thorel, Paris (FR)

(73) Assignee: BIONUCLEI, Aix en Provence (FR)

( * ) Notice: Subject to any disclaimer, the term of this patent is extended or adjusted under 35 U.S.C. 154(b) by 180 days.

(21) Appl. No.: 17/279,365

(22) PCT Filed: Oct. 1, 2019

(86) PCT No.: PCT/FR2019/052321
§ 371 (c)(1),
(2) Date: Mar. 24, 2021

(87) PCT Pub. No.: WO2020/070437
PCT Pub. Date: Apr. 9, 2020

(65) Prior Publication Data
US 2021/0401686 A1 Dec. 30, 2021

(30) Foreign Application Priority Data
Oct. 1, 2018 (FR) ..................... 1859066

(51) Int. Cl.
| | | |
|---|---|---|
| A61K 8/02 | (2006.01) | |
| A61K 8/19 | (2006.01) | |
| A61K 8/81 | (2006.01) | |
| A61Q 17/04 | (2006.01) | |
| A61Q 19/08 | (2006.01) | |
| B82Y 5/00 | (2011.01) | |

(52) U.S. Cl.
CPC .............. *A61K 8/19* (2013.01); *A61K 8/8176* (2013.01); *A61Q 17/04* (2013.01); *A61K 2800/413* (2013.01); *B82Y 5/00* (2013.01)

(58) Field of Classification Search
CPC ........ A51Q 17/04; A61K 9/14; A61K 9/0014; A61K 8/19; A61K 2800/437; A61K 2800/413; A61K 6/822; A61K 6/824; A61K 8/0241; A61Q 17/04; A61Q 19/00; B01J 23/8437; B01J 23/745
See application file for complete search history.

(56) References Cited

U.S. PATENT DOCUMENTS

| | | | |
|---|---|---|---|
| 2012/0021027 A1 | 1/2012 | Hodgson et al. | |
| 2014/0030339 A1* | 1/2014 | Leblanc | A61Q 17/04 424/617 |
| 2016/0008246 A1* | 1/2016 | Norman | A61K 8/29 424/60 |

FOREIGN PATENT DOCUMENTS

| | | |
|---|---|---|
| CN | 102658116 B | 1/2014 |
| JP | 2001048731 A | 2/2001 |
| JP | 2001220338 A * | 8/2001 |
| JP | 2010080002 A * | 4/2010 |
| JP | 2010090001 A | 4/2010 |
| JP | 2010090002 A | 4/2010 |
| WO | 2015025297 A1 | 2/2015 |

OTHER PUBLICATIONS

Y. Astuti et al 2016 IOP Conf. Ser.: Mater. Sci. Eng. 107 012006 (Year: 2016).*
Klinkova et al. Barium Bismuth Oxides with alpha, gamma, epsilon-Bi2O3 Structures. 2007. Russian Journal of Inorganic Chemistry . vol. 52, No. 11. pp. 1666-1674. (Year: 2007).*
Dinesh et al. Synthesis of Fe-doped Bi2O3 nanocatalyst and its sonophotocatalytic activity on synthetic dye and real textile wastewater. Jan. 20, 2016. Environ Sci Pollut Res. vol. 23. pp. 20100-20110. (Year: 2016).*
Materials Explorer. Bi2O3. Date retrieved Aug. 10, 2023. <https://next-gen.materialsproject.org/materials/mp-23262>. (Year: 2023).*
Dai et al. Low Fe-doped Bi2O3 photocatalyst with long wavelength response: Crystalline transition and mechanisms by first-principles calculation. Journal of Alloys and Compounds. vol. 563. (2013). pp. 80-84 (Year: 2013).*
Molak et al. Synthesis and characterization of electrical features of bismuth manganite and bismuth ferrite: effects of doping in cationic and anionic sublattice: Materials for applications. Progress in Crystal Growth and Characterization of Materials. vol. 64. Issue 1. (2018). pp. 1-22. (Year: 2018).*
Hu et al. Iron-Doped Bismuth Tungstate with an Excellent Photocatalytic Performance. Mar. 26, 2018. ChemCatChem. vol. 10. pp. 3040-3048. DOI: 10.1002/cctc.201701965. (Year: 2018).*
International Search Report (and English translation) and Written Opinion of the International Searching Authority for International Application No. PCT/FR2019/052321 mailed on Oct. 28, 2019.
Dai, Yunrong et al., "Low Fe-doped $Bi_2O_3$ photocatalyst with long wavelength response: Crystalline transition and mechanisms by first-principles calculation," Journal of Alloys and Compounds, Elsevier Sequoia, Lausanne, CH, vol. 563, Feb. 26, 2013, pp. 80-84.
Dinesh, G Kumaravel et al., "Synthesis of Fe-doped $Bi_2O_3$ nanocatalyst and its sonophotocatalytic activity on synthetic dye and real textile wastewater," Environmental Science and Pollution Research International, Ecomed, Landsberg, DE, vol. 23, No. 20, Jan. 20, 2016, pp. 20100-20110.
Malmros, Gunnar "The Crystal Structure of alpha-$Bi_2O_3$," Acta Chemica Scandinavica vol. 24, Jan. 1, 1970, pp. 384-396.
Govintha, Viruthagiri et al., "Visible Light Mediated Photocatalytic Activity of Cobalt Doped $Bi_2O_3$ Nanoparticles," Journal of Materials Research and Technology, vol. 8, No. 1, Jan. 1, 2019, pp. 127-133.

* cited by examiner

*Primary Examiner* — Tracy Liu
(74) *Attorney, Agent, or Firm* — HESLIN ROTHENBERG FARLEY & MESITI P.C.

(57) ABSTRACT

The present invention relates to a topical composition creating a photonic barrier from ultraviolet radiation to visible radiation, comprising bismuth oxide colloids $Bi_2O_3$ in crystalline form doped with a metal.

20 Claims, 3 Drawing Sheets

PHOTONIC BARRIER FOR TOPICAL USE, COMPRISING BISMUTH OXIDE COLLOIDS

CROSS REFERENCE TO RELATED APPLICATIONS

This application is a national stage filing under section 371 of International Application No. PCT/FR2019/052321 filed on Oct. 1, 2019, and published on Apr. 9, 2020 as WO 2020/070437, which claims priority to French Application No. 1859066, filed on Oct. 1, 2018. The entire contents of WO 2020/070437 are hereby incorporated herein by reference.

The invention relates to a photonic barrier ranging from UV to visible radiation, more specifically a topical composition containing doped bismuth oxide colloids, in particular bismuth oxide α-$Bi_2O_3$, optionally in the form grafted with a polymer and their use.

The field of use of the present invention relates in particular to the field of cosmetics and medical devices, and more particularly that of protection against electromagnetic radiation.

It is well known that ultraviolet A (UV-A; 400-315 nm) account for 95% of UV rays that hit the surface of the Earth. They cause premature aging of the skin by producing free radicals and therefore a phenomenon of oxidative stress.

Ultraviolet B (UV-B; 315-280 nm) are more energetic than UV-A. However, they are partially filtered by the atmosphere and represent 5% of UV rays received on Earth. They are responsible for actinic erythema and also help to accelerate the aging of the skin by producing cellular oxidative stress resulting from the generation of free radicals.

Ultraviolet C (UV-C; 280-100 nm) is even more energetic than UV-B. On the other hand, they are almost completely filtered by the ozone layer and are not the subject of special attention in the field of sun filters.

Visible ultraviolet rays (UV-V; 400-490 nm) are less energetic than other ultraviolet rays. However, they are ultraviolet rays that penetrate the skin most deeply, reaching the reticular dermis and possibly causing significant cellular damage.

For the purposes of the invention, the term "visible ultraviolet or UV-V" denotes visible radiation close to ultraviolet radiation, preferably from 400 to 490 nm, advantageously from 400 to 450 nm, even more advantageously from 400 to 420 nm.

All UV rays are involved in the mechanisms of carcinogenesis.

In general, the sun protection compositions comprise at least one sun filter which may be organic or inorganic.

By way of example, and without limitation, organic sunscreens may be compounds belonging to the following families: aminobenzoates, cinnamates, salicylates, benzophenones, phenyl benzotriazoles, etc.

Mineral sun filters include in particular titanium dioxide ($TiO_2$) and zinc oxide (ZnO).

This type of protection makes it possible to limit the harmful effects of ultraviolet rays.

The various sun filters mentioned above do not cover the whole range of ultraviolet rays to which humans may be exposed. Indeed, this is because a filter is generally active for a restricted range of wavelengths. For example, titanium dioxide and zinc oxide do not filter all UV-A, or an organic ethylhexyl triazone filter only filters UV-B.

As regards more specifically protection by filtration against visible UV-V or ultraviolet rays, that is to say, visible radiation close to ultraviolet radiation, preferably from 400 to 490 nm, advantageously from 400 to 450 nm, even more advantageously from 400 to 420 nm, it has so far not been the subject of effective specific development.

In order to remedy this problem, sunscreen compositions generally combine several sunscreens and antioxidants which neutralize the downstream effects of UV rays, mainly UV-A (400 to 315 nm) and UV-V (400 to 490 nm). It can be a mixture of organic and/or mineral sun filters.

However, the combination of several filters with many excipients can cause problems of interactions between the different elements, affecting the effectiveness of the protection. On the other hand, organic filters can be easily absorbed through the skin. However, some are suspected of having deleterious effects on human health and, in particular, of being endocrine disruptors. Finally, the various filters are susceptible to degradation which, here again, limits sun protection, or even causes harm to the body.

The problem which the invention proposes to solve is that of developing a composition intended to protect the skin from ultraviolet radiation and which does not have the drawbacks presented above.

Bismuth oxide is generally used in the field of medical imaging, as an X-ray opacifier, or in the field of energy, for example in the electrolyte of fuel cells.

The applicant noticed, quite unexpectedly, that the non-amorphous form of bismuth oxide, that is to say, the crystalline form, can be used in a cosmetic composition, in particular as a ultraviolet radiation filter.

According to a first aspect, the present invention relates to a topical composition comprising bismuth oxide colloids $Bi_2O_3$ in crystalline form doped with a metal.

This composition creates a photonic barrier ranging from ultraviolet radiation to visible radiation, preferably from 200 to 490 nm, advantageously from 200 to 450 nm, even more advantageously from 200 to 420 nm.

Thanks to the presence of bismuth oxide colloids $Bi_2O_3$ doped in crystalline form, this composition provides photonic protection by blocking part of the electromagnetic radiation that is significantly larger than filters on the market. Therefore, the present invention provides an undeniable advantage over the compositions of the prior art which require the use of several organic and/or mineral filters to block the same range of wavelengths, in particular UV-C and UV-V rays.

According to the invention, colloids refer to particles in crystalline form. They can also be called quantum dots. In a liquid medium, for example in an aqueous medium, the colloids form a colloidal suspension or a colloidal dispersion.

According to a preferred embodiment, the colloids denote nanostructures or nanocrystals.

Bismuth oxide colloids $Bi_2O_3$ can be synthesized according to conventional techniques, for example by the so-called "bottom up" approach of precursor growth. This synthetic route, commonly used in the field of nanomaterials, implements a nucleation step and a growth step from isolated atoms. It makes it possible to control the size of the colloids.

Bismuth oxide colloids $Bi_2O_3$ can be synthesized from conventional precursors such as bismuth oxalates, namely $Bi_2(C_2O_4)_3$ or $Bi(C_2O_4)OH$, or bismuth nitrate, $Bi(NO_3)_3$.

According to a particular embodiment, the synthesis of the $Bi_2O_3$ colloids can be carried out in a basic medium, for example in the presence of sodium hydroxide.

According to another particular embodiment, the synthesis of the $Bi_2O_3$ colloids can also be carried out in the presence of compounds such as nitric acid and/or polyvinylpyrrolidone and/or glycerin.

Advantageously, the synthesis of the $Bi_2O_3$ colloids according to the invention can be carried out in water.

The $Bi_2O_3$ crystals thus obtained may be treated by:
precipitation; and/or
washing, in particular by filtration; and/or
calcination.

As already indicated, the applicant noticed that the bismuth oxide colloids can act as an agent for blocking electromagnetic radiation, advantageously from 200 nm to 420 nm, preferably ultraviolet radiation, in particular when they are applied to the skin.

According to their morphological symmetry characteristics and their physical properties, crystals can be classified into crystal systems.

Bismuth oxide $Bi_2O_3$ can have different crystallographic (polymorphic) phases with different thermal, conductive and optical properties, for example:
the $\alpha$ phase; and
the tetragonal $\beta$ phase;
the $\gamma$ phase with a centered cubic structure;
the $\delta$ phase with face-centered cubic structure.

The $\alpha$ phase crystallizes in a monoclinic type network whose lattice parameters are: a=5.84 Å; b=8.15 Å; c=7.50 Å; $\beta$=112.97°; Z=4 in the $P2_{1/c}$ space group. This phase exhibits ordered vacancies with a quarter of the free oxygen sites.

Depending on the synthesis or temperature conditions, it is possible to promote one or the other of these phases.

Unexpectedly, the doped bismuth oxide colloids, advantageously of monoclinic form, even more advantageously of monoclinic form of alpha phase, exhibit a blocking effect over almost the entire ultraviolet range, i.e., at wavelengths wave 200 and 420 nm.

According to a particular embodiment, the composition according to the invention comprises bismuth oxide colloids $Bi_2O_3$ present only in monoclinic crystalline form.

According to a particular embodiment, the composition according to the invention comprises bismuth oxide colloids $Bi_2O_3$ present only in a phase monoclinic crystalline form.

In other words, the composition according to the invention lacks bismuth oxide colloids $Bi_2O_3$:
of $\beta$, $\gamma$, and $\delta$ phase; and/or
of tetragonal, centered cubic and face-centered cubic forms According to an essential characteristic of the invention, the bismuth oxide colloids are doped with a doping agent, such as a metal.

For the purposes of the invention, the term "doping" denotes the substitution of a bismuth atom by a metal atom, in the crystal lattice.

According to the invention, the doping consists in carrying out the synthesis of the bismuth oxide colloids $Bi_2O_3$, in particular by "bottom up", and in the presence of a precursor of the doping agent or the doping agent.

Doping within the meaning of the invention is different from conventional doping which consists first of all of synthesizing the oxide colloids, then of subsequently mixing them with the precursor of the doping agent.

According to the invention, doping does not change the configuration of the crystal form. In other words, the X-ray powder diffraction pattern of $\alpha\text{-}Bi_2O_3$ colloids (alpha phase and monoclinic lattice) is exactly overlaps with that of $\alpha\text{-}Bi_2O_3$ colloids (alpha phase and monoclinic lattice) doped with a metal according to the invention.

On the contrary, in the prior art, doping $\alpha\text{-}Bi_2O_3$ colloids with an element, in particular a metal, modifies the crystalline form. It follows that the colloids are not only in the form of the alpha phase, but in the form of a mixture of the alpha, gamma and/or delta phases.

According to a particular embodiment, the metal is chosen from the group comprising alkali metals, alkaline earth metals, lanthanides, actinides, transition metals, poor metals, metalloids and their assemblies. Advantageously, it is a transition metal.

For example, the doping of bismuth oxide colloids can be implemented with iron, manganese, magnesium, copper, chromium, nickel or even zinc, optionally with the exception of potassium. or calcium.

Advantageously, the metal is iron.

In general, this dopant represents 0.01 to 5% by mass relative to the mass of $Bi_2O_3$ (before grafting with the biocompatible polymer), more advantageously 0.01 to 0.15%.

Doping bismuth oxide colloids with a metal, preferably iron, inhibits the photocatalytic activity of the colloids. The inhibition of this activity lies in a separation of the crystal meshes which then prevents the transfer of electrons.

In addition to the electromagnetic radiation blocking function, the doped bismuth oxide colloids can also provide antioxidant, antibacterial, bactericidal, antibiofilm, fungicide and antiviral properties to the cosmetic composition according to the invention.

X-ray crystallography, also called radiocrystallography or X-ray diffractometry, makes it possible to study the structure of a crystalline material on an atomic scale. This technique is based on the physical phenomenon of X-ray diffraction. For example, a diffractometer having a copper source may be used.

The diffraction pattern thus forms a true signature of the crystalline form of a compound. This signature is specific to the crystalline form of the compound. It takes the form of a list of positional peaks at angle $2\theta$ (2-theta).

According to a preferred embodiment of the invention, the doped bismuth oxide colloids are advantageously in monoclinic form, even more advantageously in a monoclinic form of alpha, alpha —$Bi_2O_3$ or -$\alpha\text{-}Bi_2O_3$ phases.

In a particular embodiment, the doped $Bi_2O_3$ colloids are grafted with a biocompatible polymer.

The bismuth oxide colloids used in the invention are not comparable to the particles of the prior art, for example those disclosed in documents JP 2010-090001 and JP 2010-090002. These documents disclose undoped and/or ungrafted particles, whose crystalline phase ($\alpha$, $\beta$, $\gamma$, etc.) is incidentally not specified.

For the purposes of the invention, the term "biocompatible" denotes a compound that is cytocompatible with the skin, the mucous membranes and the integuments and which exhibits a cytotoxicity of less than 15%, preferably less than 10%, towards human epidermis reconstructed in vitro (SkinEthic RHE model). In other words, this compound remains almost neutral with respect to cell viability.

This cytocompatibility can be evaluated by the cell viability test, whose reagent is the tetrazolium salt MTT (3-(4,5-dimethylthiazol-2-yl)-2,5-diphenyl tetrazolium bromide).

The MTT test is a colorimetric method for the detection of mitochondrial activity that allows the cytotoxic power of a constituent to be assessed. It is based on the reduction of the tetrazolium ring contained in the reagent, by the mitochondrial succinate dehydrogenase of active living cells, to formazan. This forms a precipitate in the mitochondria which is purple in color.

In practice, after application of the test element to epidermis for 42 minutes, followed by a post-treatment incubation of 42 hours, cell viability is assessed by measuring the activity of mitochondrial succinate dehydrogenase in living cells. This enzyme transforms MTT into crystals of blue formazan. After dissolution of these crystals, a spectrophotometric reading of the optical density is carried out at 550 nm. Absorbance measurements are proportional to the number of living cells.

The biocompatible polymer may have hydrophilic or lipophilic properties. Advantageously, it is a hydrophilic polymer.

This biocompatible polymer may be advantageously hydrophilic and chosen from the group comprising polyvinylpyrrolidone (PVP) and its copolymers such as triacontanyl-PVP, PVP-eicosene or PVP-vinylacetate, polyvinyl acetate, polyvinyl alcohol, polyvinyl chloride, styrenics, polyamides, acrylates, polyesters, polybutenes, polysaccharides such as pullulan, arabinoxylans, cellulose, chitin, chitosan, xanthan gum, dextran, welan gum, gellan gum, arabic gum, hyaluronic acid, cellulose and its derivatives, starch, diutan, proteins and their constituents such as sericin and amino acids, fatty acids, phospholipids, phosphoglycerides, triglycerides, silane coupling agents and mixtures thereof.

Grafting prevents the penetration of $Bi_2O_3$ colloids into the skin by improving the bioadhesiveness between the colloids and the skin. In other words, improving the adhesion of colloids to the skin limits or prevents their penetration into the skin.

Through physical or mechanical interactions and chemical interactions, the biocompatible polymer acts as a bioadhesive on the skin. Thus, the composition according to the invention adheres to the skin and is not removed by simple washing with water or sea water.

The bioadhesion of the biocompatible polymer, which occurs by creating chemical bonds with the skin, successively leads to:
  intimate contact between the biocompatible polymer and the skin. This intimate contact is favored by the wetting of the bioadhesive biocompatible polymer on the skin and/or its swelling, and
  filling the cracks and fine lines of the skin with the bioadhesive biocompatible polymer.

The biocompatible polymer also makes it possible to improve the dispersion of the $Bi_2O_3$ colloids in an aqueous medium, and therefore to obtain a homogeneous distribution when the composition according to the invention is applied to the skin. Therefore, the composition comprising the colloids according to the invention is advantageously a composition in which the colloids are in suspension.

Grafting with a biocompatible polymer also makes it possible to improve the stability of the $Bi_2O_3$ colloids over time and/or at acidic pH, in particular at the pH of the skin between 5.2 and 7. In the absence of grafting, the $Bi_2O_3$ colloids, especially alpha-$Bi_2O_3$, are unstable over time and/or deteriorate more rapidly at pH below 7.

The concept of grafting, or functionalization, of colloids is part of the general knowledge of a person skilled in the art. Grafting, or functionalization, corresponds to the formation of covalent bonds, for example, between the biocompatible polymer and the surface of the colloids. These are not heart/shell type colloids.

The biocompatible polymer can provide lipophilic or hydrophilic properties to the colloids.

In general, the composition may comprise doped $Bi_2O_3$ colloids, advantageously grafted, between 1 and 60% by mass relative to the mass of the composition, more advantageously between 20 and 50%. This is the percentage by mass of the doped, and advantageously grafted, $Bi_2O_3$ colloids.

Advantageously, the doped $Bi_2O_3$ colloids of the composition may comprise between 60 and 100% of doped bismuth oxide colloids in alpha crystalline form, preferably of doped monoclinic alpha crystalline form, advantageously between 80 and 100%, preferably 100%. These doped colloids in alpha crystalline form are advantageously grafted with a biocompatible polymer. In other words, according to this embodiment, 60 to 100% of the doped $Bi_2O_3$ colloids of the composition are in the alpha crystalline form, preferably 80 to 100%, more preferably 100%.

The $Bi_2O_3$ colloids are advantageously spherical in shape.

The $Bi_2O_3$ colloids, advantageously in the alpha crystalline phase, preferably the monoclinic alpha crystalline phase, doped and grafted or not, have a size advantageously between 0.5 and 1000 nm, more advantageously between 0.5 and 100 nm, and even more advantageously of the order of 30 nm.

The size is measured by XRD (X-ray diffraction) which is a technique for measuring the size of crystals in the solid state.

The term "size" denotes the largest dimension of the colloids, for example the diameter in the case of colloids of spherical shape. This is the average size of grafted or ungrafted colloids. Indeed, the size of the grafted colloids, according to the present invention, is also included within the ranges of values given above.

According to a particular embodiment, the composition may also comprise a lipophilic and/or hydrophilic mineral sunscreen. This filter may, in particular, be chosen from the group comprising titanium oxides ($TiO_2$), zinc (ZnO), iron ($Fe_2O_3$), zirconium ($ZrO_2$), silicon ($SiO_2$), manganese (for example, MnO), aluminum ($Al_2O_3$), cerium ($Ce_2O_3$), and mixtures thereof.

Advantageously, the mineral sunscreen is in colloidal or particle form.

According to another particular embodiment, the composition may also comprise a lipophilic and/or hydrophilic organic sunscreen. This filter may, in particular, be chosen from the group comprising the INCI designations: Camphor benzalkonium Methosulfate, Homosalate, Butyl Methoxydibenzoylmethane, Phenylbenzimidazole-Sulfonic Acid, Terephthalylidene Dicamphor Sulfonic Acid, Butyl Methoxydibenzoylmethane, Benzylidene Camphor Sulfonic Acid, Octocrylene, Polyacrylamidomethyl Benzylidene Camphor, Ethylhexyl Methoxycinnamate, PEG-25 PABA, Isomamyl p-Methoxycinnamate, Ethylhexyl Triazone, Drometrizole Trisiloxane, Diethylhexyl Butamido Triazone, 4-Methylbenzylidene Camphor, 3-Benzylidene Camphor, Ethylhexyl Salicylate, Ethylhexyl Dimethyl PABA or Octyl Dimethyl PABA, Benzophenone-4/Benzophenone-5, Methylene Bis-Benzotriazolyl Tetramethylbutylphenol, Disodium Phenyl Dibenzimidazole Tetrasulfonate, Bis-Ethylhexyloxyphenol Methoxyphenyl Triazine, Polysilicone-15, Diethylamino Hydroxybenzoyl Hexyl Benzoate and mixtures thereof.

According to a particular embodiment, the topical composition is intended for therapeutic use.

According to another particular embodiment, the topical composition is not intended for therapeutic use.

Advantageously, the composition according to the invention is a sunscreen composition It may be in the form of an aqueous suspension of colloids preferably doped with a metal, and advantageously grafted, of a suspension of colloids preferably doped with a metal, and advantageously grafted, in an oil phase or an emulsion of the water-in-oil or oil-in-water type, comprising colloids preferably doped with a metal, and advantageously grafted.

The biocompatible polymer may have hydrophilic or lipophilic properties.

When the composition comprises an oil-type dispersant, the biocompatible polymer, grafted onto the bismuth oxide colloids, is advantageously lipophilic.

When the composition comprises a water-type dispersant, the biocompatible polymer, grafted onto the bismuth oxide colloids, is advantageously hydrophilic.

The composition according to the invention advantageously comprises a biocompatible polymer between 2 and 20% by mass relative to the mass of the composition, more advantageously between 4 and 10%. These percentages include the biocompatible polymer optionally grafted onto the $Bi_2O_3$ colloids, doped preferably with a metal.

According to a particular embodiment, the composition according to the invention may further comprise at least one additive chosen from the group comprising dispersants, humectants, stabilizers, and pH regulators.

Advantageously, the dispersant is water and/or oil.

Preferably, the oil is chosen from the group comprising hydrocarbon oils of vegetable origin (sunflower, corn, soybean, grape seed, sesame, hazelnut, castor oil, etc.), hydrocarbons (linear or branched) of mineral or synthetic origin (paraffin oil, etc.), silicone oils (polymethylsiloxanes, cyclopolydimethylsiloxanes, etc.), fluorinated oils, and mixtures thereof.

According to another embodiment, the oil may be a hydrocarbon oil of animal origin.

The dispersant is advantageously water.

In practice, the composition according to the invention advantageously comprises between 20 and 80% water and/or oil by mass relative to the mass of the composition, more advantageously between 40 and 60%.

Advantageously, the humectant is chosen from the group comprising glycerol, urea, lactic acid and mixtures thereof.

The composition according to the invention advantageously comprises between 5 and 25% humectant by mass relative to the mass of the composition, advantageously between 7 and 15%.

The humectant helps prevent the composition from drying out too quickly after it is applied to the skin. It also helps hydrate the skin. It may also contribute to controlling the viscosity of the composition according to the invention, with the aim of optimizing its spread on the skin.

Advantageously, the stabilizer is chosen from the group comprising sorbitan monolaurate, guar gum, xanthan gum, and mixtures thereof.

The composition according to the invention advantageously comprises between 0.5 and 5% stabilizer by mass relative to the mass of the composition, more advantageously between 1 and 3%.

The stabilizer makes it possible to control the viscosity of the composition.

Advantageously, the pH regulator is chosen from the group comprising citric acid, acetic acid, adipic acid, ascorbic acid, boric acid, fumaric acid, glycolic acid, lactic acid, malic acid, uric acid and mixtures thereof.

The composition according to the invention advantageously comprises between 0.1 and 1% pH regulator by mass relative to the mass of the composition, more advantageously between 0.2 and 0.5%.

The pH regulator makes it possible to maintain the pH of the composition at a physiological value.

It improves the stability of the composition by adjusting its pH when it is applied to the skin, that is to say, when it is applied to an acidic medium.

A person skilled in the art will know how to adapt the amount of pH regulator so that the composition has a pH advantageously between 5.2 and 7.

According to a particular embodiment, the composition according to the invention is advantageously free of preservative, which is not the case with the majority of conventional sunscreen compositions.

As already mentioned, the cosmetic composition is a topical composition. It has many advantages, among which:
    a simple formulation containing few components, advantageously in an aqueous medium,
    increased effectiveness in protecting against a broad spectrum of ultraviolet radiation (UV-C, UV-B, UV-A and UV-V), such composition being likened to a solar paint,
    a very high sun protection factor,
    little or no penetration into the stratum corneum (outermost cell layer of the skin), thus protecting sensitive and atopic skin,
    good adhesion to the skin, allowing long-lasting sun protection.

According to a preferred embodiment, the composition according to the invention comprises, by mass relative to the mass of the composition:
    between 1 and 60% of doped bismuth oxide colloids, advantageously in the monoclinic alpha form, $\alpha\text{-}Bi_2O_3$, and advantageously grafted with a biocompatible polymer;
    between 2 and 20% of structuring biocompatible polymer, preferably polyvinylpyrrolidone (PVP);
    between 5 and 25% humectant, preferably glycerol;
    between 0.5 and 5% stabilizer, preferably sorbitan monolaurate;
    between 0.1 and 1% pH regulator, preferably citric acid; and
    between 20 and 80% water and/or oil.

According to a preferred embodiment, the composition according to the invention comprises, by mass relative to the mass of the composition:
    between 1 and 60% of doped bismuth oxide colloids, advantageously present only in the monoclinic alpha form, $\alpha\text{-}Bi_2O_3$, and advantageously grafted with a biocompatible polymer;
    between 2 and 20% of structuring biocompatible polymer, preferably polyvinylpyrrolidone (PVP);
    between 5 and 25% of humectant, preferably glycerol;
    between 0.5 and 5% of stabilizer, preferably sorbitan monolaurate;
    between 0.1 and 1% of pH regulator, preferably citric acid; and
    between 20 and 80% water and/or oil.

Advantageously, the composition according to the invention can be stored in a medium lacking carbon dioxide, and advantageously lacking oxygen. These storage conditions make it possible to extend the duration of use of the composition according to the invention.

The present invention also relates to the use of doped bismuth oxide colloids $Bi_2O_3$, advantageously grafted with a biocompatible polymer, as an ultraviolet filter, advantageously of UV-A, UV-B, UV-C and UV-V, preferably for the 200-420 nm. wavelength spectrum. This use is particularly suitable when the colloids are contained in a topical cosmetic composition.

The invention and the advantages resulting therefrom will emerge more clearly from the following figures and examples, given in order to illustrate the invention and not in a limiting manner.

1/ SYNTHESIS OF DOPED BISMUTH OXIDE COLLOIDS

A bismuth oxide precursor, such as bismuth nitrate pentahydrate and an iron precursor, such as iron chloride, are mixed with water, nitric acid and sodium hydroxide then sealed in an autoclave.

The reaction mixture is then precipitated then washed by filtration before undergoing a calcination step at a temperature between 100 and 500° C.

Once the reaction mixture reaches the set temperature, the temperature is maintained until crystallization of the doped bismuth oxide.

Spherical bismuth oxide nanocrystals, 7 nm in diameter, are collected.

Figure 5:
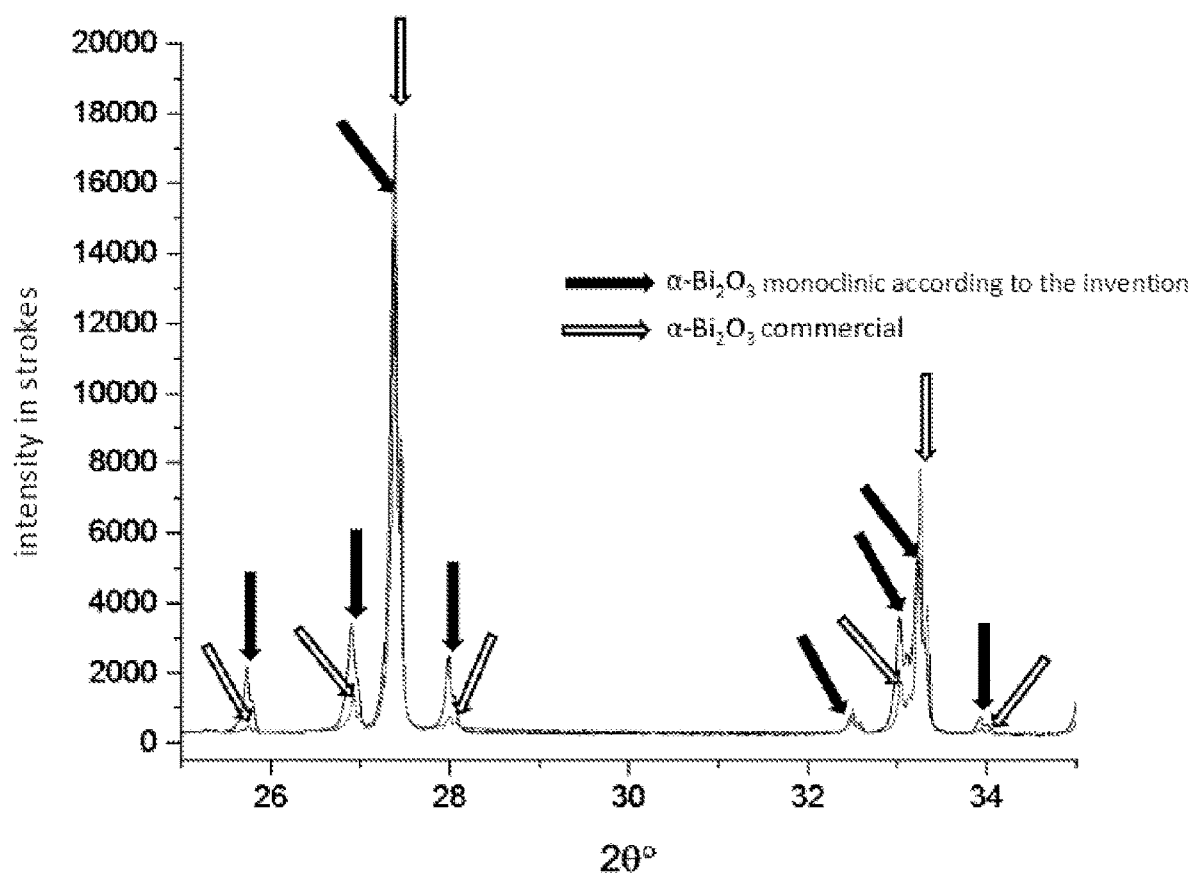
FIG. 5 represents an X-ray powder diffraction diagram comparing the peaks of $\alpha$-$Bi_2O_3$ colloids (monoclinic alpha crystal phase) according to the invention, and commercial $\alpha$-$Bi_2O_3$ colloids.

The X-ray powder diffraction pattern comparing the peaks of $Bi_2O_3$ colloids, present only in alpha phase crystalline form in a monoclinic lattice according to the invention ($\alpha$-$Bi_2O_3$), and of commercial $\alpha$-$Bi_2O_3$ colloids, is shown in FIG. 5.

The results show the presence of additional and/or different peaks for the commercial $\alpha$-$Bi_2O_3$ colloids compared to the colloids according to the invention. Commercial $\alpha$-$Bi_2O_3$ colloids are a mixture of the alpha and gamma phases of bismuth oxide. Indeed, the peak at about 30° 2θ is not compatible with an alpha phase but with a gamma phase, and the minor peaks around the main peak at about 27.5° 2θ are not expected in a gamma phase but are found in an alpha phase.

In contrast, the colloids according to the invention are pure and do not exhibit additional peaks that can be attributed to a crystalline phase of bismuth oxide other than the alpha phase. In other words, the colloids according to the invention correspond only to the crystalline form in alpha phase in a monoclinic array.

2/ $\alpha$-$Bi_2O_3$, $TiO_2$ AND ZNO COLLOIDS

The absorption spectra of monoclinic $\alpha$-$Bi_2O_3$ colloids, $TiO_2$ particles and ZnO particles were compared.

To that end, the following compounds were used in water:
(a) $TiO_2$ colloids (40 nm with aggregates of the order of 250 nm measured by DLS) in the form of anatase, the $TiO_2$ being grafted with 2% m PVP,
(b) ZnO colloids (15 nm) grafted with 2% m PVP,
(c) $\alpha$-$Bi_2O_3$ colloids doped with iron (colloids in alpha phase form and in a monoclinic array; 30 nm by XRD and 40 nm by DLS) grafted with 2% m PVP.

% m denotes the percentage by mass of PVP relative to the mass of $TiO_2$, ZnO or $\alpha$-$Bi_2O_3$ doped with iron.

The grafting of the colloids is carried out in a conventional manner, for example, in a solution of water and ethanol containing the colloids and the polymer to be grafted (PVP).

The wavelength produced by the diffractometer used to measure the size by XRD corresponds to the Cu-$K_\alpha$ line equal to 1.54 Å. The other parameters used are as follows: acceleration voltage: 40 kV; current: 40 mA; Bragg-Brentano geometry.

For size measurements by DLS, the conditions are as follows: wavelength equal to 633 nm; 90° detector; 25° C. The sample analyzed is diluted (0.5 g/L) in cocosilicone oil in a 1 mm tank.

2-a) Mass Extinction Coefficient

The average mass extinction coefficients (c) of these compounds based on the wavelength were obtained from measurements made using a conventional spectrophotometer. The average mass coefficient corresponds to the average of measurements carried out in tanks of 10 μm, 100 μm and 0.1 cm thickness for solutions of 10% m (100 g/L), 0.75% m (7.5 g/L) and 0.05% m (0.5 g/L) respectively. The mass coefficient is obtained from the Beer-Lambert formula:

$$\varepsilon = A/lC$$

where A is the measured absorbance, l (cm) is the optical path through the sample, and C (g/L) is the mass concentration of the sample.

Figure 2:
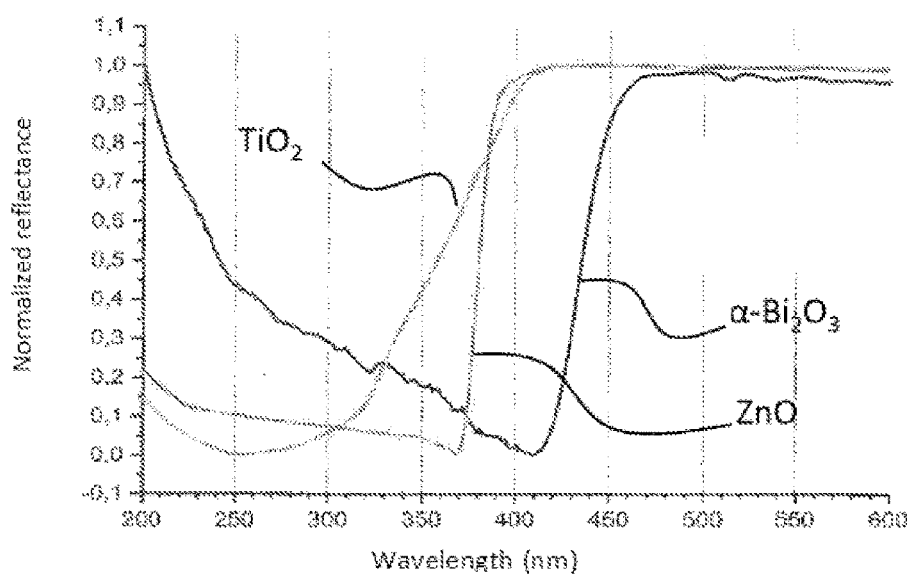
FIG. 2 represents the reflectance for colloidal solutions of $TiO_2$, ZnO and $\alpha$-$Bi_2O_3$, doped based on the wavelength.

The results are shown in FIG. 2.

$TiO_2$ particles exhibit a higher average mass coefficient in the UV-B region (280-315 nm). However, doped $\alpha$-$Bi_2O_3$ colloids (alpha phase and monoclinic array) exhibit a UV-A (315-400 nm) absorption capacity that is significantly greater than that of $TiO_2$. The average mass coefficient of ZnO remains lower, regardless of the wavelength.

2-b) Protection Against Ultraviolet Rays

The sun protection factor (SPF), the UV-A protection factor (FP-UVA) and the critical wavelength of solutions (a), (b) and (c), previously mentioned, were calculated from the following equations, and for a 10 μm thick tank:

$$SPF = \frac{\int_{290}^{400} E_\lambda \cdot S_\lambda \cdot d\lambda}{\int_{290}^{400} E_\lambda \cdot S_\lambda \cdot T_\lambda \cdot d\lambda}$$

$$SP-UVA = \frac{\int_{320}^{400} E_\lambda \cdot S_\lambda \cdot d\lambda}{\int_{320}^{400} E_\lambda \cdot S_\lambda \cdot T_\lambda \cdot d\lambda}$$

$$R = \frac{\int_{290}^{\lambda} \log \frac{1}{T_\lambda} \cdot d\lambda}{\int_{290}^{400} \log \frac{1}{T_\lambda} \cdot d\lambda}$$

in which:

$E_\lambda$ denotes the erythemal action spectrum (value between 0 and 1) of the wavelength $\lambda$. This is the amount at which UV radiation at wavelength $\lambda$ is likely to cause erythema on the skin.

$S_\lambda$ denotes the spectral irradiance at the wavelength $\lambda$.

$T_\lambda$ denotes the transmittance of the sample at the wavelength $\lambda$.

$d_\lambda$ denotes an integration variable.

The values $E_\lambda$ and $S_\lambda$ are known.

The critical wavelength corresponds to the wavelength for which the ratio R is greater than or equal to 0.9. In other words, it is the wavelength for which the integral of the spectrum curve $$(\int_{290}^{\lambda} \log 2/\tau_\lambda \cdot d_\lambda)$$

is equal to 90% of the integral between 290 and 400 nm.

The critical wavelengths of the compounds $TiO_2$, ZnO and $\alpha\text{-}Bi_2O_3$ are respectively equal to 368 nm, 362 nm and 382 nm.

Only the $\alpha\text{-}Bi_2O_3$ compound alone makes it possible to achieve a critical wavelength greater than 370 nm.

Figure 3:
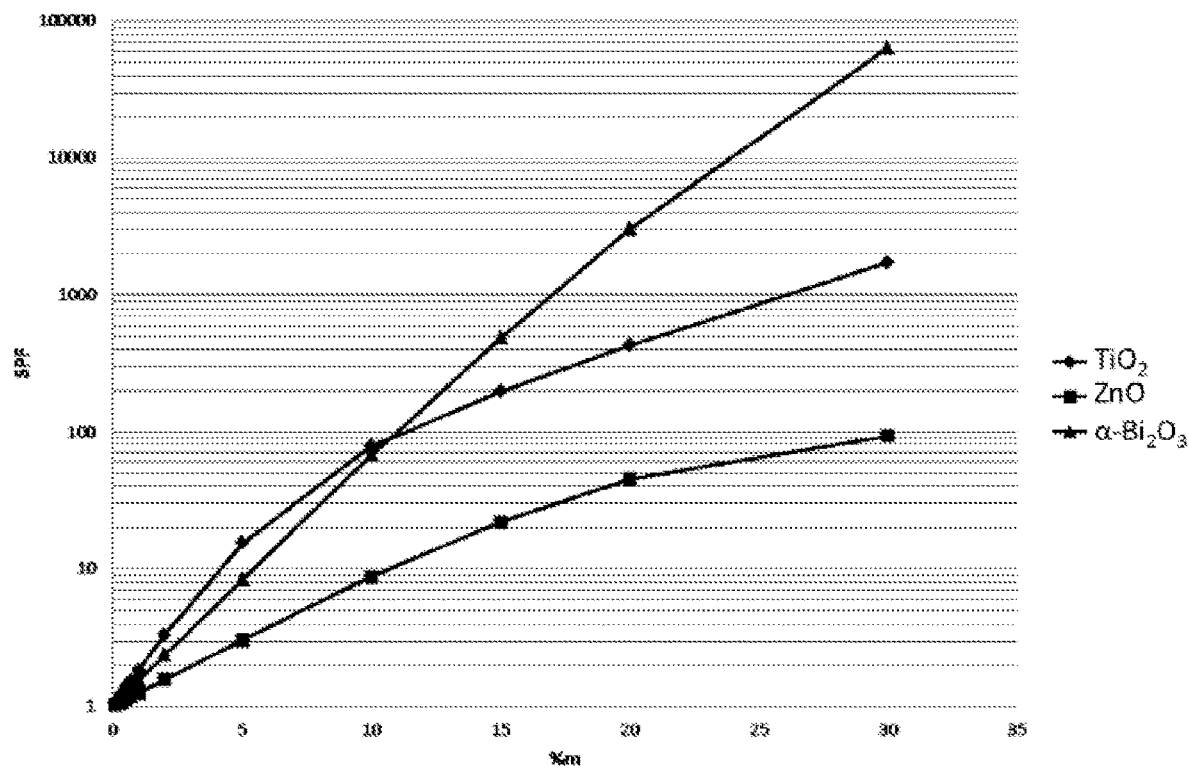
FIG. 3 represents the sun protection factor (SPF) of compositions containing grafted particles of $TiO_2$, ZnO and $\alpha$-$Bi_2O_3$, doped based on their percentage by mass.

FIG. 3 represents the sun protection factor (SPF) of particles grafted with $TiO_2$, ZnO and $\alpha\text{-}Bi_2O_3$ (alpha phase and monoclinic array), doped with iron based on their mass percentage (0.1 to 30% m) in a 10-μm tank.

These curves are used to determine the amount of sun filter necessary to achieve a predetermined sun protection factor (SPF). Table 1 specifies the mass percentages necessary to achieve an SPF of 20, 30, 50 or 100 from the data in FIG. 3.

TABLE 1

Mass percentage (% m) of mineral filter ($TiO_2$, ZnO, $\alpha\text{-}Bi_2O_3$ doped with iron) based on the sun protection factor (SPF).

| | SPF 20 | SPF 30 | SPF 50 | SPF 100 |
|---|---|---|---|---|
| $TiO_2$ (% m) | 5.6 | 6.66 | 8.26 | 11.2 |
| ZnO (% m) | 14.5 | 17 | 21 | 31.7 |
| Doped $\alpha\text{-}Bi_2O_3$ (% m) | 7.06 | 8.04 | 9.3 | 11 |

Tables 2 and 3 list the UVA protection factor (SP-UVA) and the SPF: SP-UVA ratio for SPFs of 50 and 100.

TABLE 2

UVA protection factor (SP-UVA) and SPF:SP-UVA ratio for an SPF of 50.

| | SP-UVA | SPF:SP-UVA |
|---|---|---|
| $TiO_2$ (8.26% m) | 5.22 | 9.57 |
| ZnO (21% m) | 8.34 | 6 |
| Doped $\alpha\text{-}Bi_2O_3$ (9.3% m) | 21.21 | 2.36 |

TABLE 3

UVA protection factor (SP-UVA) and SPF:SP-UVA ratio for an SPF of 100.

| | SP-UVA | SPF:SP-UVA |
|---|---|---|
| $TiO_2$ (11.2% m) | 8.73 | 11.46 |
| ZnO (31.7% m) | 13.27 | 7.54 |
| $\alpha\text{-}Bi_2O_3$ (11% m) | 36.74 | 2.72 |

It follows from FIG. 3 that the effectiveness of the mineral filters studied is as follows: $TiO_2$>$Bi_2O_3$>ZnO for concentrations between 0.1 and 10% m; and $Bi_2O_3$>$TiO_2$>ZnO for concentrations greater than 10% m.

Figure 1:
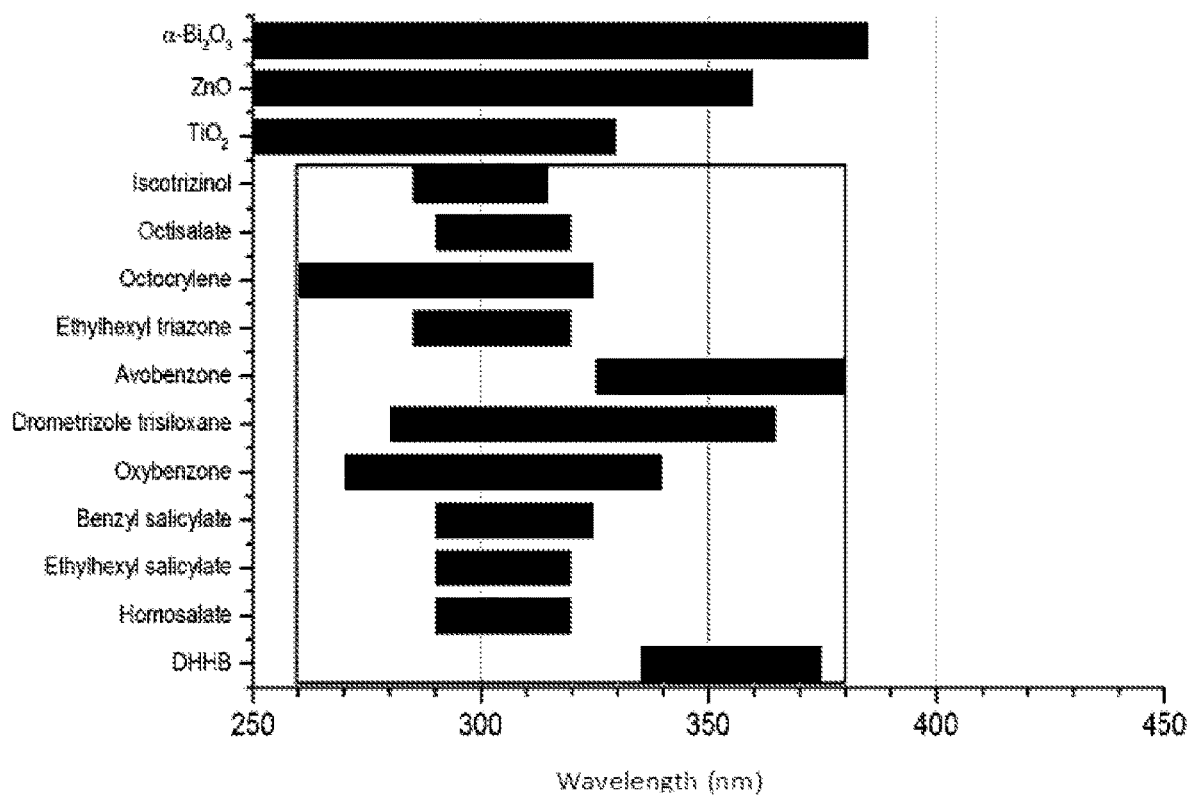
FIG. 1 represents the absorption spectrum of organic and mineral sun filters and according to a preferred embodiment of the invention (doped $\alpha$-$Bi_2O_3$).

On the other hand, $\alpha\text{-}Bi_2O_3$ colloids (alpha phase and monoclinic array), doped with iron, exhibit a greater absorption range than that of conventional mineral filters (FIG. 1). Thus, they make it possible not to have to resort to a mixture of organic and/or inorganic filters.

3/ PHOTOCATALYTIC ACTIVITY

The photocatalytic activity of mineral UV filters is assessed by monitoring the degradation of methylene blue in the presence of various filters or a control and UV radiation.

The mineral filters tested are oxides. More precisely, they are ZnO, and $\alpha\text{-}Bi_2O_3$, doped with iron according to the invention.

In detail, 10 μL of 50 g/L oxide suspension in water is added to 4990 μL of $1E^{-5}$ mol·$L^{-1}$ solution of methylene blue in water. A control is also made by adding 10 μL of water in place of the oxide suspension in 4990 μL of a $1E^{-5}$ mol·$L^{-1}$ solution of methylene blue in water. The solutions are placed in the dark for 30 minutes in order to achieve the adsorption equilibrium of the dye at the surface of the oxide being studied.

The absorbance of the solutions is then measured between 540 nm and 710 nm, which corresponds to the adsorption of methylene blue. These measurements constitute the time t=0 minutes. The solutions are subsequently stirred under UV lighting.

Absorbance measurements at 15, 30, 45, 60, 90 and 120 minutes are taken.

The area under the curve between 540 nm and 710 nm makes it possible to measure the relative amount of methylene blue compared to the measurement t=0 min.

Figure 4:
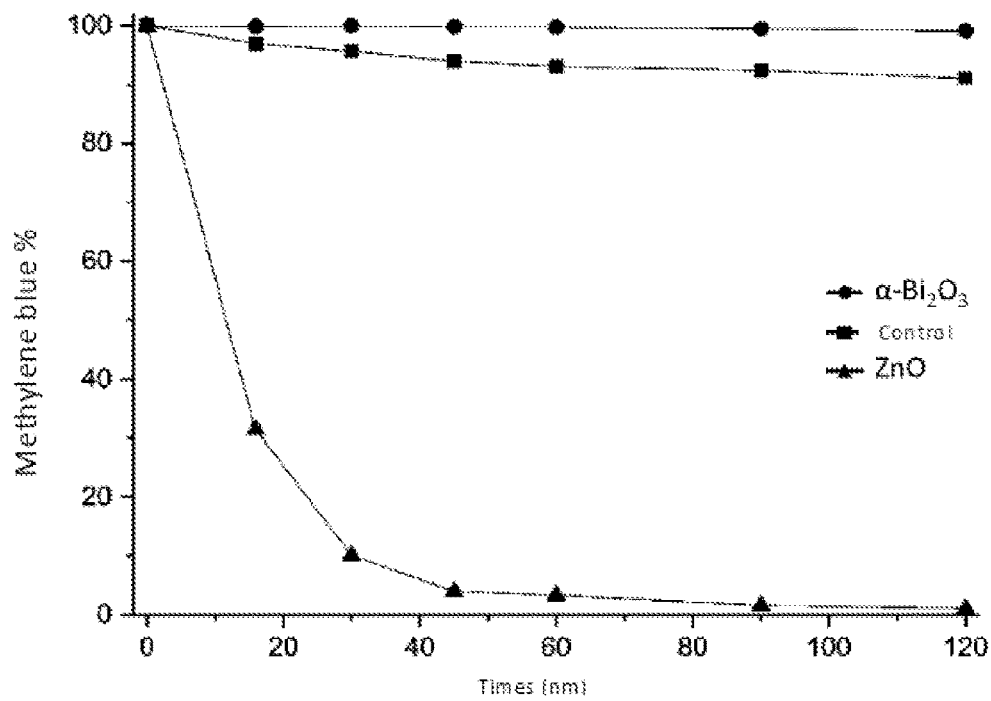
FIG. 4 represents the analysis of the photocatalytic activity of a mineral sunscreen, according to a preferred embodiment of the invention (doped $\alpha$-$Bi_2O_3$) and a control.

The results are shown in FIG. 4.

The results show that zinc oxide has significant photocatalytic activity with 90% degradation of methylene blue within 30 minutes.

The control shows a degradation of about 10% which is not due to photocatalysis, but to photo-degradation of the dye under UV.

In the case of $\alpha\text{-}Bi_2O_3$ colloids (alpha phase and monoclinic array), doped according to the invention, the degradation is almost zero, which demonstrates an absence of photocatalytic activity of the oxide. The photo-degradation of the dye also seems limited compared to the control because only 2% of the methylene blue was degraded. This phenomenon is due to the absorption of part of the UV radiation and the reduction of ROS by the $\alpha\text{-}Bi_2O_3$ colloids doped with iron according to the invention.

4/ COSMETIC COMPOSITION ACCORDING TO THE INVENTION

A composition according to the invention was prepared and compared with commercial solar compositions (Table 4).

TABLE 4

Characteristics of commercial compositions compared to the invention

| Composition | UV filter (quantity) | SPF | Blocked UV-V |
|---|---|---|---|
| Actinica Lotion | Organic | 50+ | 3.44% |
| ISDIN Spot Prevent | Organic | 50+ | 0% |
| Dermina | Organic and mineral | 50 | 19.81% |
| Mineral crème Bépanthène Soleil | Mineral | 50+ | 16.59% |
| Sun Burn | Organic | 70+ | 0% |
| Invention | α-$Bi_2O_3$ doped with iron (alpha phase and monoclinic array) | 50+ | 25.93% |

In general, Table 4 shows that the compositions containing inorganic UV filters are the most effective for blocking UV-V (visible UV: 400-450 nm).

The composition according to the invention has the best effectiveness over the entire UV range (UV-C, UV-B, UV-A and UV-V).

Skin penetration tests have shown that compositions comprising organic filters penetrate the skin more deeply than compositions comprising a mixture of organic and inorganic filters or only inorganic filters.

The best results are obtained for the composition according to the invention. It penetrates the skin much less than the other compositions. As already indicated, this effect is certainly due to the improvement in the bioadhesiveness of the colloids due to their grafting with a biocompatible polymer.

The invention claimed is:

1. A topical composition creating a photonic barrier against electromagnetic radiation ranging from ultraviolet radiation to visible radiation comprising bismuth oxide colloids $Bi_2O_3$ in monoclinic form of alpha phase having a crystal lattice, wherein the bismuth oxide colloids are doped with iron, wherein the iron represents 0.01 to 0.15% by mass relative to the mass of $Bi_2O_3$, and is present in the crystal lattice, and wherein the iron-doped bismuth oxide colloids have reduced photocatalytic activity as compared to corresponding bismuth oxide colloids that have not been doped with iron.

2. The composition according to claim 1, wherein bismuth oxide colloids present in the composition consist of bismuth oxide in monoclinic alpha phase form, a-$Bi_2O_3$.

3. The composition according to claim 1, wherein the monoclinic form corresponds to the following mesh parameters: a=5.84 Å; b=8.15 Å; c=7.50 Å; β=112.97°; Z=4 in the $P2_{1/c}$ space group.

4. The composition according to claim 1, wherein the bismuth oxide colloids are grafted with a biocompatible polymer.

5. The composition according to claim 1, wherein the bismuth oxide colloids are grafted with a biocompatible polymer chosen from the group consisting of polyvinylpyrrolidone (PVP) and its copolymers, polyvinyl acetate, polyvinyl alcohol, polyvinyl chloride, styrenics, polyamides, acrylates, polyesters, polybutenes, polysaccharides, fatty acids, phospholipids, phosphoglycerides, triglycerides, silane coupling agents and mixtures thereof.

6. The composition according to claim 1, wherein the bismuth oxide colloids are grafted with a biocompatible polymer and the bismuth oxide colloids grafted with a biocompatible polymer are present in an amount between 10 and 60% by mass relative to the mass of the composition.

7. The composition according to claim 1, wherein the doped $Bi_2O_3$ colloids comprise between 60 and 100% of doped bismuth oxide colloids in alpha crystalline form.

8. The composition according to claim 1, wherein the doped bismuth oxide colloids have a size ranging from 0.5 nm to 1000 nm.

9. The composition according to claim 1, wherein the composition further comprises:
   at least one lipophilic and/or hydrophilic mineral sunscreen chosen from the group consisting of: titanium oxides ($TiO_2$), zinc (ZnO), iron ($Fe_2O_3$), zirconium ($ZrO_2$), silicon ($SiO_2$), manganese (e.g., MnO), aluminum ($Al_2O_3$), cerium ($Ce_2O_3$), and mixtures thereof; and/or
   at least one lipophilic and/or hydrophilic organic sunscreen selected from the group consisting of the INCI designations: Camphor benzalkonium Methosulfate, Homosalate, Butyl Methoxydibenzoylmethane, Phenylbenzimidazole-Sulfonic Acid, Terephthalylidene Dicamphor Sulfonic Acid, Butyl Methoxydibenzoylmethane, Benzylidene Camphor Sulfonic Acid, Octocrylene, Polyacrylamidomethyl Benzylidene Camphor, Ethylhexyl Methoxycinnamate, PEG-25 PABA, Isomamyl p-Methoxycinnamate, Ethylhexyl Triazone, Drometrizole Trisiloxane, Diethylhexyl Butamido Triazone, 4-Methylbenzylidene Camphor, 3-Benzylidene Camphor, Ethylhexyl Salicylate, Ethylhexyl Dimethyl PABA or Octyl Dimethyl PABA, Benzophenone-4/Benzophenone-5, Methylene Bis-Benzotriazolyl Tetramethylbutylphenol, Disodium Phenyl Dibenzimidazole Tetrasulfonate, Bis-Ethylhexyloxyphenol Methoxyphenyl Triazine, Polysilicone-15, Diethylamino Hydroxybenzoyl Hexyl Benzoate and mixtures thereof.

10. The composition according to claim 1, wherein the composition further comprises at least one additive selected from the group consisting of dispersants, humectants, stabilizers, and pH regulators.

11. The composition according to claim 1, wherein the composition is a topical sunscreen composition.

12. A method of: protecting skin from ultraviolet radiation; protecting skin from free radicals; or combating aging of skin; the method comprising applying to the skin a composition comprising iron doped bismuth oxide colloids $Bi_2O_3$ in monoclinic form of alpha phase having a crystal lattice, wherein the iron represents 0.01 to 0.15% by mass relative to the mass of $Bi_2O_3$, and is present in the crystal lattice, and wherein the iron-doped bismuth oxide colloids have reduced photocatalytic activity as compared to corresponding bismuth oxide colloids that have not been doped with iron.

13. The method according to claim 12, wherein the method is a method of protecting skin from ultraviolet radiation.

14. The method according to claim 12, wherein the method is a method of protecting skin from free radicals.

15. The method according to claim 12, wherein the method is a method for combating aging of skin.

16. The method according to claim 12, wherein the composition is a topical composition creating a photonic barrier against electromagnetic radiation ranging from ultraviolet radiation to visible radiation, and wherein the iron doped bismuth oxide colloids represent more than 10% by mass relative to the mass of the composition.

17. The method according to claim 12, wherein the aging or the free radicals is (are) photo-induced.

18. An antioxidant composition comprising iron-doped bismuth oxide colloids $Bi_2O_3$ in monoclinic form of alpha phase having a crystal lattice, wherein the iron represents 0.01 to 0.15% by mass relative to the mass of $Bi_2O_3$, and is present in the crystal lattice, and wherein the iron-doped bismuth oxide colloids have reduced photocatalytic activity as compared to corresponding bismuth oxide colloids that have not been doped with iron.

19. The composition according to claim 1, wherein the iron doped bismuth oxide colloids represent more than 10% by mass relative to the mass of the composition.

20. The composition according to claim 1, additionally comprising stabilizer in an amount between 0.5 and 5% by mass relative to the mass of the composition, wherein all stabilizer in the composition is selected from the group consisting of sorbitan monolaurate, guar gum, xanthan gum, and mixtures thereof.

\* \* \* \* \*